United States Patent [19]

Unger

[11] Patent Number: 5,681,542
[45] Date of Patent: Oct. 28, 1997

[54] COMPOSITIONS COMPRISING A BIOCOMPATIBLE GAS AND A POLYMER FOR MAGNETIC RESONANCE IMAGING

[75] Inventor: Evan C. Unger, Tucson, Ariz.

[73] Assignee: ImaRx Pharmaceutical Corp., Tucson, Ariz.

[21] Appl. No.: 472,864

[22] Filed: Jun. 7, 1995

Related U.S. Application Data

[62] Division of Ser. No. 465,862, Jun. 6, 1995, which is a division of Ser. No. 465,431, Jun. 5, 1995, which is a division of Ser. No. 251,484, May 31, 1994, which is a division of Ser. No. 960,591, Oct. 13, 1992, Pat. No. 5,368,840, which is a continuation-in-part of Ser. No. 507,125, Apr. 10, 1990, abandoned.

[51] Int. Cl.$^6$ ...................................................... A61B 5/055
[52] U.S. Cl. .................. 424/9.3; 424/9.36; 424/9.52; 436/173; 514/6; 514/54; 514/57
[58] Field of Search ......................... 424/9.3, 9.36, 424/9.52; 436/173, 806; 128/653.4, 654; 514/6, 54, 57, 59

[56] References Cited

U.S. PATENT DOCUMENTS

| | | | |
|---|---|---|---|
| 4,069,306 | 1/1978 | Rothman | 424/4 |
| 4,225,592 | 9/1980 | Lakatos et al. | 424/180 |
| 4,586,511 | 5/1986 | Clark, Jr. | 128/653 |
| 4,647,447 | 3/1987 | Gries et al. | 424/9 |
| 4,678,667 | 7/1987 | Meares et al. | 424/85 |
| 4,719,098 | 1/1988 | Weinmann et al. | 424/9 |
| 4,729,892 | 3/1988 | Beall | 424/9 |
| 4,775,522 | 10/1988 | Clark, Jr. | 424/9 |
| 4,804,529 | 2/1989 | Bardy et al. | 424/9 |
| 4,822,594 | 4/1989 | Gibby | 424/9 |
| 4,826,673 | 5/1989 | Dean et al. | 424/9 |
| 4,830,849 | 5/1989 | Osterholm | 424/2 |
| 4,838,274 | 6/1989 | Schweighardt | 128/654 |
| 4,849,210 | 7/1989 | Widder | 424/9 |
| 4,865,836 | 9/1989 | Long, Jr. | 424/5 |
| 4,871,716 | 10/1989 | Longo et al. | 514/2 |
| 4,898,734 | 2/1990 | Mathiowitz et al. | 424/426 |
| 4,925,648 | 5/1990 | Hansen et al. | 424/1.1 |
| 4,927,623 | 5/1990 | Long, Jr. | 424/5 |
| 4,933,441 | 6/1990 | Gibby | 536/112 |
| 4,963,344 | 10/1990 | Gries et al. | 424/9 |
| 4,986,980 | 1/1991 | Jacobsen | 424/9 |
| 4,996,041 | 2/1991 | Arai et al. | 424/9 |
| 5,000,960 | 3/1991 | Wallach | 424/450 |
| 5,021,236 | 6/1991 | Gries et al. | 424/9 |
| 5,094,848 | 3/1992 | Brixner | 424/85.91 |
| 5,174,987 | 12/1992 | Takaichi et al. | 424/9 |
| 5,186,924 | 2/1993 | Fishman | 424/9 |
| 5,215,680 | 6/1993 | D'Arrigo | 252/307 |
| 5,230,883 | 7/1993 | Kornguth et al. | 424/9 |
| 5,236,694 | 8/1993 | Antich et al. | 424/9 |
| 5,315,997 | 5/1994 | Widder et al. | 28/653.4 |

FOREIGN PATENT DOCUMENTS

| | | |
|---|---|---|
| 0 118 281 | 9/1984 | European Pat. Off. . |
| 0 184 899 | 6/1986 | European Pat. Off. . |
| 0 186 974 A1 | 7/1986 | European Pat. Off. . |

(List continued on next page.)

OTHER PUBLICATIONS

Clanton et al., *Radiology*, vol. 149, p. 238 (1983) (abstract).
Clanton et al., *Radiology*, vol. 153, p. 159 (1984) (abstract).

(List continued on next page.)

*Primary Examiner*—Gary E. Hollinden
*Attorney, Agent, or Firm*—Woodcock Washburn Kurtz Mackiewicz & Norris

[57] ABSTRACT

Novel contrast media for use in magnetic resonance imaging are described. Such contrast media are comprised of biocompatible polymers either alone or in admixture with one or more contrast agents such as paramagnetic, superparamagnetic or proton density contrast agents. Additionally, the polymers or polymer and contrast agent admixtures may be mixed with one or more biocompatible gases to increase the relaxivity of the resultant preparation, and/or with other components. In a preferable embodiment, the contrast medium is hypoosmotic.

105 Claims, 4 Drawing Sheets

FOREIGN PATENT DOCUMENTS

| | | |
|---|---|---|
| 228692 | 12/1986 | European Pat. Off. . |
| 284549 | 3/1988 | European Pat. Off. . |
| 0 409 351 A1 | 1/1991 | European Pat. Off. . |
| WO 85/04330 | 10/1985 | WIPO . |
| WO 85/05554 | 12/1985 | WIPO . |
| WO 89/11874 | 12/1989 | WIPO . |
| WO 90/01953 | 8/1990 | WIPO . |

OTHER PUBLICATIONS

Hahn et al., *Radiology*, vol. 164, pp. 37–41 (1987).
Hahn et al., *Magn. Reson. Imaging*, vol. 6, p. 78 (1988) (abstract).
D.M. Kean and M.A. Smith, *Magnetic Resonance Imaging: Principles and Applicatioins*, (Williams and Wilkins, Baltimore 1986).
Kornmesser et al., *Magn. Reson. Imaging*, vol. 6, p. 124 (1988) (abstract).
Laniado et al., *AJR*, vol. 150, pp. 817–821 (1988).
Mattrey et al., *AJR*, vol. 148, pp. 1259–1263 (1987).
Newhouse et al., *Radiology*, vol. 142(P), p. 246 (1982) (abstract).
Runge et al., *Radiology*, vol. 147, pp. 789–791 (1983).
Runge et al., *Physiol. Chem. Phys. Med. NMR*, vol. 16, pp. 113–122 (1984).
Tscholakoff et al., *AJR*, vol. 148, pp. 703–709 (1987).
Weinreb et al., *J. Comput. Assist. Tomogr.*, vol. 8, pp. 835–838 (1984).
Wesbey et al., *Radiology*, vol. 149, pp. 175–180 (1983).
Wesbey et al., *Magn. Reson. Imaging*, vol. 3, pp. 57–64 (1985).
Widder et al., *AJR*, vol. 149, pp. 839–843 (1987).
Williams et al., *Radiology*, vol. 161(P), p. 315 (1986) (abstract).
Young et al., *CT*, vol. 5, pp. 543–547 (1981).
Bailey et al., *Poly(ethylene oxide)* (Academic Press, NY 1976).
Blow et al., *FEBS. Lett.*, vol. 94, pp. 305–310 (1978).
Laurent, *Eur. J. Biochem.*, vol. 21, pp. 498–506 (1971).
Pilgrimm et al., *Chemical Abstracts*, vol. 112, p. 380, No. 51778y (1990).
S. Deiana et al., *Inorganica Chemica Acta*, vol. 46, pp. 249–253 (1980).
S. Deiana et al., *Interaction of Transition–Metal With Polygalacturonic Acid: A Potentiometric Study* (Elsevier Scientific Publishing Co., Amsterdam, 1982).
Atkins et al., *Biopolymers*, vol. 12, pp. 1865–1878 (1973).
Atkins et a., *Biopolymers*, vol. 12, pp. 1879–1887 (1973).
Mihashi, *Pharmaceutical J.*, vol. 81, pp. 1000–1002 (1961).
Guyton, Arthur C., *Textbook of Medical Physiology*, Chapters 4 and 33, 6th Ed., W.B. Saunders Company, Philadelphia, PA (1981).
Braybrook et al., "Effect of PH on the Nuclear Magnetic Resonance Relaxivity ... ", *Drug Design and Delivery*, vol. 4, pp. 93–95 (Harwood Academic, Great Britain 1989).

COMPOSITIONS COMPRISING A BIOCOMPATIBLE GAS AND A POLYMER FOR MAGNETIC RESONANCE IMAGING

CROSS REFERENCE TO RELATED APPLICATION

This application is a divisional of Ser. No. 08/465,862, filed Jun. 6, 1995 which is a divisional of Ser. No. 08/465,431, filed Jun. 5, 1995, which is a divisional of Ser. No. 08/251,484, filed May 31, 1994, which is a divisional of Ser. No. 07/960,591, filed Oct. 13, 1992, now U.S. Pat. No. 5,368,840, which is a continuation-in-part of Ser. No. 07/507,125, filed Apr. 10, 1990, abandoned.

BACKGROUND OF THE INVENTION

1. Field of the Invention

This invention relates to the field of magnetic resonance imaging, more specifically to the use of polymers or polymers in combination with contrast agents and/or gases as contrast media for magnetic resonance imaging.

2. Description of the Prior Art

There are a variety of imaging techniques that have been used to diagnose disease in humans. One of the first imaging techniques employed was X-rays. In X-rays, the images produced of the patients' body reflect the different densities of body structures. To improve the diagnostic utility of this imaging technique, contrast agents are employed to increase the density between various structures, such as between the gastrointestinal tract and its surrounding tissues. Barium and iodinated contrast media, for example, are used extensively for X-ray gastrointestinal studies to visualize the esophagus, stomach, intestines and rectum. Likewise, these contrast agents are used for X-ray computed tomographic studies to improve visualization of the gastrointestinal tract and to provide, for example, a contrast between the tract and the structures adjacent to it, such as the vessels or lymph nodes. Such gastrointestinal contrast agents permit one to increase the density inside the esophagus, stomach, intestines and rectum, and allow differentiation of the gastrointestinal system from surrounding structures.

Magnetic resonance imaging (MRI) is a relatively new imaging technique which, unlike X-rays, does not utilize ionizing radiation. Like computed tomography, MRI can make cross-sectional images of the body, however MRI has the additional advantage of being able to make images in any scan plane (i.e., axial, coronal, sagittal or orthogonal). Unfortunately, the full utility of MRI as a diagnostic modality for the body, particularly in the abdominal and pelvic region, is hampered by the lack of an effective gastrointestinal contrast agent. Without such an agent, it is often difficult using MRI to differentiate the intestines from, for example, adjacent soft tissues and lymph nodes. If better contrast agents were available, the overall usefulness of MRI as an imaging agent would improve, and the diagnostic accuracy of this modality in the gastrointestinal region would be greatly enhanced.

MRI employs a magnetic field, radiofrequency energy and magnetic field gradients to make images of the body. The contrast or signal intensity differences between tissues mainly reflect the T1 and T2 relaxation values and the proton density (effectively, the free water content) of the tissues. In changing the signal intensity in a region of a patient by the use of a contrast medium, several possible approaches are available. For example, a contrast medium could be designed to change either the T1, the T2 of the proton density.

A paramagnetic contrast agent such as Gd-DTPA causes longitudinal relaxation to shorten T1. This increases the signal intensity on T1-weighted images. A superparamagnetic contrast agent such as ferrites works predominantly on transverse relaxation causing a shortening of T2 and decreasing signal intensity on T2-weighted images. A contrast agent could also work by altering the proton density, specifically by decreasing the amount of free water available that gives rise to the signal intensity.

Agents that increase the signal intensity from the lumen compared to the native contents are termed positive contrast agents. A number of these have been examined as contrast agents for MRI. These include fats and oils (Newhouse et al., *Radiology*, 142 (P):246 (1982)), which increase signal as a result of their short T1, long T2 and high intrinsic proton density, as well as various paramagnetic agents that increase signal by decreasing the T1 of water protons. Examples of such paramagnetic agents include Gd-DTPA (Kornmesser et al., *Magn. Reson. Imaging*, 6:124 (1988), and Laniado et al., *AJR*, 150:817 (1988)), Gd-DOTA (Hahn et al. *Magn. Reson. Imaging*, 6:78 (1988)), Gd-oxalate (Runge, V. M. et al., *Radiology*, 147:789 (1983)), Cr-EDTA (Runge, V. M. et al., *Physiol. Chem. Phys. Med. NMR*, 16:113 (1984)), Cr-Trisacetylacetonate (Clanton et al., *Radiology*, 149:238 (1983)), ferric chloride (Young et al., *CT*, 5:543 (1981)), ferrous gluconate (Clanton et al., *Radiology*, 153:159 (1984)), ferric ammonium citrate and ferrous sulfate (Wesbey et al., *Radiology*, 149:175 (1983) and Tscholakoff et al., *AJR*, 148:703 (1987)) as well as iron complexes (Wesbey et al., *Magn. Reson. Imaging*, 3:57 (1985) and Williams et al., *Radiology*, 161:315 (1986)).

Alternatively, agents that decrease the signal intensity from the lumen are termed negative contrast agents. Examples include particulate iron oxides (Hahn et al., *Radiology*, 164:37 (1987), Widder et al., *AJR*, 149:839 (1987)) which decrease signal via T2 shortening, as well as gas-evolving materials (Weinreb et al., *J. Comput. Assist. Tomogr*, 8:835 (1984)) and perfluorocarbons (Mattrey et al., *AJR*, 148:1259 (1987)) which act through changes in the proton density. It should be recognized that all paramagnetic substances at sufficiently high concentrations can also result in a decrease in signal intensity via T2 shortening.

The existing MRI contrast agents all suffer from a number of limitations when employed as oral gastrointestinal agents. Positive contrast agents increase the image noise arising from intrinsic peristaltic motions and motions imposed via respiration or cardiovascular action. Positive contrast agents such as Gd-DTPA are subject to the further complication that the signal intensity depends upon the concentration of the agent as well as the pulse sequence used. Absorption of contrast agent from the gastrointestinal tract complicates interpretation of the images, particularly in the distal portion of the small intestine, unless sufficiently high concentrations of the paramagnetic species are used (Kornmesser et al., *Magn. Reson. Imaging*, 6:124 (1988)). Negative contrast agents by comparison are less sensitive to variation in pulse sequence and provide more consistent contrast. However at high concentrations, particulates such as ferrites can cause magnetic susceptibility artifacts which are particularly evident in the colon where the absorption of intestinal fluid occurs and the superparamagnetic material may be concentrated. Negative contrast agents typically exhibit superior contrast to fat, however on T1-weighted images, positive contrast agents exhibit superior contrast versus normal tissue. Since most pathological tissues exhibit longer T1 and T2 than normal tissue, they will appear dark on T1-weighted and bright on T2-weighted images. This would indicate that an ideal contrast agent should appear bright on T1-weighted images and dark on T2-weighted images. None of the currently available MRI contrast media for use with the gastrointestinal tract meet these dual criteria.

Toxicity is another problem with the existing contrast agents. With any drug there is some toxicity, the toxicity generally being dose related. With the ferrites there are often symptoms of nausea after oral administration, as well as flatulence and a transient rise in serum iron. The paramagnetic contrast agent Gd-DTPA is an organometallic complex of gadolinium coupled with the complexing agent diethylene triamine pentaacetic acid. Without coupling, the free gadolinium ion is highly toxic. The peculiarities of the gastrointestinal tract, wherein the stomach secretes acids and the intestines release alkalines, raise the possibility of decoupling and separation of the free gadolinium from the complex as a result of these changes in pH during gastrointestinal use. Certainly, minimizing the dose of either gastrointestinal contrast agent, whether paramagnetic or superparamagnetic, is important for minimizing any potential toxic effects.

New and/or better contrast agents useful in magnetic resonance imaging, particularly in the imaging of the gastrointestinal tract but also in the imaging of other regions of the body such as through the vasculature, are needed. The present invention is directed to this important end.

SUMMARY OF THE INVENTION

The present invention is directed to a contrast medium useful for magnetic resonance imaging, said contrast medium comprising an aqueous solution or suspension of at least one biocompatible polymer. Optionally, the contrast medium further comprises, in admixture, contrast agents, especially paramagnetic, superparamagnetic and/or proton density contrast agents. The polymer or polymer and contrast agent admixtures may also optionally comprise, if desired, biocompatible gases, preferably gases such as air, oxygen, carbon dioxide, nitrogen, xenon, neon and/or argon, as well as other components as desired.

In a preferable embodiment, the present invention encompasses a contrast medium for use in magnetic resonance imaging comprising an aqueous solution or suspension of at least one biocompatible polymer in admixture with a contrast agent, wherein the contrast medium is hypoosmotic to the bodily fluids of the patient. In further preferable embodiments, the present invention is directed to a contrast medium comprising an aqueous solution or suspension of a biocompatible synthetic polymer in admixture with a contrast agent, a contrast medium comprising an aqueous solution or suspension of a biocompatible synthetic non-cross-linked polymer, a contrast medium consisting essentially of an aqueous solution or suspension of a biocompatible non-cross-linked polymer, and a contrast medium consisting essentially of an aqueous solution or suspension of at least one biocompatible polymer and at least one biocompatible gas.

The subject invention also pertains to a method of providing an image of an internal region of a patient, especially an image of the gastrointestinal region of the patient, said method comprising (i) administering to the patient one or more of the aforementioned contrast media, and (ii) scanning the patient using magnetic resonance imaging to obtain visible images of the region.

Further, the present invention encompasses a method for diagnosing the presence of diseased tissue in a patient, especially in the gastrointestinal region of the patient, said method comprising (i) administering to the patient one or more of the foregoing contrast media, and (ii) scanning the patient using magnetic resonance imaging to obtain visible images of any diseased tissue in the region.

These and other aspects of the invention will become more apparent from the following detailed description when taken in conjunction with the following drawings.

DETAILED DESCRIPTION OF INVENTION

Figure 1:
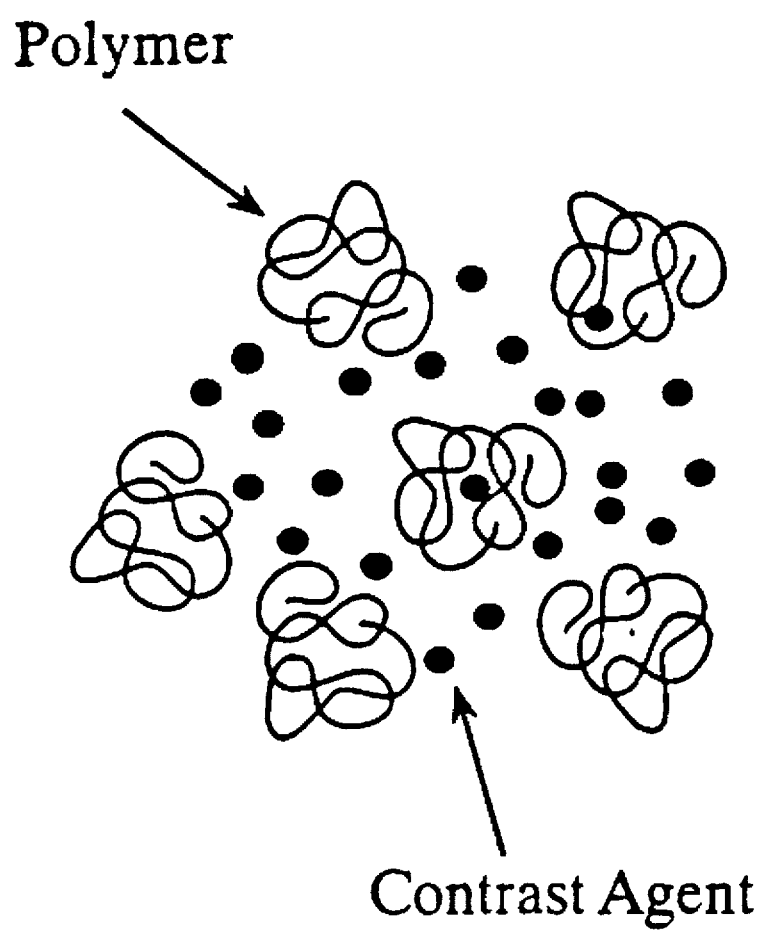
FIG. 1 is a diagrammatic view of a contrast medium in accordance with the present invention.

Any of the wide variety of biocompatible (physiologically compatible) polymers known in the art may be employed in the medium or methods of the subject invention. As will be readily apparent to those skilled in the art, there are numerous types of such polymers available. Preferably, the polymer chosen is one which has a relatively high water binding capacity. Also preferably, the polymer has limited ability for ion complexation. Where imaging of the gastrointestinal region is desired, preferably the polymer chosen is one which is not substantially absorbed from or degraded within the gastrointestinal region. The polymers useful in the present invention can be of either synthetic or natural origin. As used herein, the term polymer denotes a compound comprised of two or more repeating monomeric units, and preferably 10 or more repeating monomeric units. The polymers may be cross-linked, if desired. Preferably, however, the polymers are not cross-linked (referred to herein as non-cross-linked).

Exemplary synthetic polymers suitable for use in the present invention include polyethylenes (such as, for example, polyethylene glycol), polyoxyethylenes (such as, for example, polyoxyethylene glycol), polypropylenes (such as, for example, polypropylene glycol), pluronic acids and alcohols, polyvinyls (such as, for example, polyvinyl alcohol), and polyvinylpyrrolidone. Exemplary natural polymers suitable for use in the present invention include polysaccharides. Polysaccharides include, for example, arabinans, fructans, fucans, galactans, galacturonans, glucans, mannans, xylans (such as, for example, inulin), levan, fucoidan, carrageenan, galactocarolose, pectin (including high methoxy pectin and low methoxy pectin; with low methoxy pectin denoting pectin in which less than 40% of the carboxylic acid groups are esterified and/or amidated, and high methoxy pectin denoting pectin in which 40% or more of the carboxylic acid groups are esterified and/or amidated), pectic acid, amylose, pullulan, glycogen, amylopectin, cellulose, carboxylmethylcellulose, hydroxypropyl methylcellulose, dextran, pustulan, chitin, agarose, keratan, chondroitin, dermatan, hyaluronic acid and alginic acid, and various other homopolymers or heteropolymers such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagarose, glucuronic acid, gluconic acid, glucaric acid, galacturonic acid, mannuronic acid, guluronic acid, glucosamine, galactosamine and neuraminic acid. It is recognized that some polymers may be prepared by chemically modifying naturally occurring polymers. Such chemically modified natural polymers are to be considered within the scope of the phrase natural polymers, as used herein.

The polymers of the present invention may be employed in various shapes and forms, such as, for example, as fibers, beads, and particles. The polymers may also be of varying molecular weights, such as high molecular weight polymers (that is, equal to or greater than 30,000 weight average molecular weight) or low molecular weight polymers (that is, less than 30,000 weight average molecular weight). For reasons of diagnostic efficacy, preferably the polymers are low molecular weight polymers, more preferably having a molecular weight (weight average) of about 25,000 or less, still more preferably less than about 20,000, even more preferably less than about 15,000, and most preferably less than about 10,000. One highly preferable weight average molecular weight range is between about 25,000 and about 1,500.

Polyethylene glycol (PEG), a synthetic polymer that exhibits a high water binding capacity, is particularly preferred for use in the subject invention. As a result of their high water binding capacity and concomitant decrease in the amount of free water in solution, PEG and similar polymers serve to alter the proton density in solution. Furthermore, PEG is used for the fractional precipitation of proteins from solution, which is believed to be due to in part to the excluded volume effects caused by this polymer whereby the protein is excluded from regions of the solution occupied by the polymer and is concentrated up in the water spaces, that is, the extrapolymer spaces, between the individual molecules of the polymer. This exclusion and concentration effect is illustrated diagrammatically in FIG. 1, with the polymer being represented by the squiggly lines and the contrast agent being represented by the solid dots. Since PEG exhibits limited ability for ion complexation, it will also cause a small paramagnetic chelate such as Gd-DTPA to be concentrated such that the effective concentration and the relaxivity of the paramagnetic species will be higher in mixtures with the polymer than in the absence of the polymer. For these and other reasons, PEG, and related polymers, are particularly preferred polymers for the subject invention. PEG, as well as other synthetic polymers, may be prepared, in varying molecular weights, using conventional methodology.

Other natural polymers particularly preferred for reasons of diagnostic efficacy include polygalacturonic acid (and other polyuronic acids, such as polyglucuronic acid, polymannuronic acid, polyguluronic acid, hyaluronic acid etc.), low methoxy pectin, dextran, and cellulose. Especially preferred is low molecular weight poly-galacturonic acid and low molecular weight low methoxy pectin, especially polygalacturonic acid. Polyuronic acids such as polygalacturonic acid, and low methoxy pectin, dextran, cellulose and other such polymers, may be obtained or prepared, in varying molecular weights, using conventional techniques.

The polymers of the present invention may be employed alone, in an aqueous solution or suspension, as a contrast medium for magnetic resonance imaging. Alternatively, if desired, the polymers may be employed in admixture with conventional physiologically compatible contrast agents. By admixture, it is meant that the contrast agent is simply added to the polymer-containing medium, and is not chemically bound to the polymer by a covalent linkage. Electrostatic interactions or hydrogen bonding may, however, exist between the polymer and contrast agents, and such associations are considered to be within the ambit of the term admixture.

Numerous contrast agents are well known to those skilled in the art and include, for example, paramagnetic, superparamagnetic and proton density contrast agents.

Exemplary paramagnetic contrast agents suitable for use in the subject invention include stable free radicals (such as, for example, stable nitroxides), as well as compounds comprising transition, lanthanide and actinide elements which may, if desired, be covalently or noncovalently bound to complexing agents or to proteinaceous macromolecules. Preferable elements include Gd(III), Mn(II), Cu(II), Cr(III), Fe(II), Fe(III), Co(II), Er(II), Ni(II), Eu(III) and Dy(III). More preferably, the elements include Gd(III), Mn(II), Cu(II), Fe(II), Fe(III), Eu(III) and Dy(III), especially Mn(II) and Gd(III). Preferable complexing agents include, for example, diethylenetriamine-pentaacetic acid (DTPA), ethylene-diaminetetraacetic acid (EDTA), 1,4,7,10-tetraazacyclododecane-N, N',N',N'"-tetraacetic acid (DOTA), 1,4,7,10-tetraazacyclododecane-N,N',N"-triacetic acid (DO3A), 3,6,9-triaza-12-oxa-3,6,9-tricarboxymethylene-10-carboxy-13-phenyl-tridecanoic acid (B-19036), hydroxybenzylethylene-diamine diacetic acid (HBED), N,N'-bis(pyridoxyl-5-phosphate)ethylene diamine, N,N'-diacetate (DPDP), 1,4,7-triazacyclononane-N,N',N"-triacetic acid (NOTA), 1,4,8,11-tetraazacyclotetradecane-N,N'N",N,'"-tetraacetic acid (TETA) and kryptands (that is, macrocyclic complexes). More preferably, the complexing agents are DTPA, DOTA, DO3A and kryptands, most preferably DTPA. Preferable proteinaceous macromolecules include albumin, collagen, polyarginine, polylysine, polyhistidine, γ-globulin and β-globulin. More preferably, the proteinaceous macromolecules comprise albumin, polyarginine, polylysine, and polyhistidine. Most preferably, the paramagnetic contrast agents employed in the present invention are Mn(II)-DTPA, Mn(II)-DOTA, Mn(II)-DO3A, Mn(II)-kryptands, Gd(III)-DTPA, Gd(III)-DOTA, Gd(III)-DO3A, or Gd(III)-kryptands, especially Mn(II)-DTPA or Gd(III)-DTPA.

Exemplary superparamagnetic contrast agents suitable for use in the subject invention include ferro- or ferromagnetic compounds, such as pure iron, magnetic iron oxide (such as magnetite), γ-Fe$_2$O$_3$, manganese ferrite, cobalt ferrite and nickel ferrite. Exemplary proton density contrast agents include perfluorocarbons.

The polymer or polymer and contrast agent admixtures of the subject invention may also be employed, if desired, in admixture with biocompatible gases. In the case of both negative and positive contrast agents, such gases often serve to increase the efficacy of the contrast medium. The gas can be bubbled through the medium using conventional techniques. Any biocompatible gas is suitable for use in the present invention. Numerous such gases are well known to those skilled in the art. Exemplary biocompatible gases include, air, oxygen, carbon dioxide, nitrogen, xenon, neon and argon, the foregoing list referencing, of course, the most common isotope of such gases.

Wide variations in the amounts of the polymer, and the contrast agent and/or gas, can be employed in the contrast medium of the invention. Preferably, however, the polymer is present in a concentration of at least about 0.01% to about 1%, by weight, more preferably, between about 0.05% and about 50%, by weight, even more preferably between about 0.5% and about 40%, and generally most preferably between about 0.5% and about 5%, by weight. Of course, as those skilled in the art would recognize, within these parameters the optimum polymer concentration will be influenced by the molecular weight of the polymer, its water binding capacity, as well as other characteristics of the particular polymer employed. Also, preferably, in the case of paramagnetic and proton density contrast agents, the contrast agent is present in a concentration of at least about 0.1 millimolar, more preferably between about 0.5 and about 2 millimolar, most preferably between about 0.7 and about 1 millimolar. In the case of superparamagnetic agents, the concentration is preferably at least about 1 micromolar, more preferably between about 5 and about 50 micromolar, and most preferably is about 10 micromolar. Where gas is employed, preferably at least about 20 psi is bubbled through the solution for about one minute prior to administration, more preferably between about 30 or about 50 psi, most preferably about 40 psi.

If desired, in addition, the contrast medium may further comprise a physiologically compatible suspending or viscosity increasing agent, referred to herein collectively as a suspending agent. The phrase suspending agent, as used herein, denotes a compound that assists in providing relative uniformity or homogeneity to the contrast medium. A number of such agents are available, including xanthum gum, acacia, agar, alginic acid, aluminum monostearate, bassotin, karaya, gum arabic, unpurified bentonite, purified bentonire, bentonire magma, carbomer 934P, calcium carboxymethylcellulose, sodium carboxymethylcellulose, carboxymethylcellulose sodium 12, carrageenan, cellulose (microcrystalline), dextran, gelatin, guar gum, hydroxyethylcellulose, hydroxypropylcellulose, hydroxypropylmethylcellulose, magnesium aluminum silicate, methylcellulose, pectin, casein, gelatin, polyethylene oxide, polyvinyl alcohol, povidone, propylene glycol, alginate, silicon dioxide, silicon dioxide colloidal, sodium alginate and other alginates, and tragacanth. Of the foregoing suspending agents, xanthan gum is the most preferred. As those skilled in the art would recognize, wide ranges of suspending agent can be employed in the contrast medium of the invention, as needed or desired. Preferably, however, the suspending agent is present in an amount of at least about 0.05% by weight, more preferably at least about 0.1% by weight, and generally less than about 1% by weight, even more preferably less than about 0.5% by weight.

As mentioned above, in a preferable embodiment, the contrast medium is hypoosmotic. By "hypoosmotic" (or "hypoosmolarity"), as used herein, it is meant a contrast medium which has less osmolarity, measured in milliosmoles per liter of solution, than the bodily fluids of the patient. Osmolarity is a term that is well known in the art, and is discussed for example, in Guyton, Arthur C., *Textbook of Medical Physiology*, Chapters 4 and 33, 6th ed., W. B. Saunders Company, Philadelphia, Pa. (1981), the disclosures of which are hereby incorporated herein by reference, in their entirety. The osmolarity of normal biological fluids of a patient, which would surround the contrast medium in use (for example, the fluids in and behind the membranous tissues forming or adjacent to the gastrointestinal tract walls, where gastrointestinal use of the contrast medium is contemplated), have an osmolarity between 280 and 305 milliosmoles/liter. The osmolarity of the hypoosmotic contrast medium of the present invention is typically less than 280 milliosmoles/liter, preferably between about 200 and about 270 milliosmoles/liter, more preferably between about 220 and about 260 milliosmoles/liter, and most preferably between about 250 to about 260 milliosmoles/liter.

The hypoosmotic nature of this preferred embodiment of the invention serves to prevent or greatly minimize the flow of water into the region where the contrast medium is being employed. Such an influx of water has been found to be deleterious to the most effective use of the contrast medium. Specifically, it has been found that such an influx of water may serve to increase the motility of the contrast medium through the area to be imaged thereby lessening the time period available to the radiologist to carry out an effective scan. It may also cause undesired distension (overdistention) in the area in which the contrast agent is administered resulting in a distorted image, and may produce patient discomfort such as, for example, diarrhea and gastrointestinal upset, in the case of gastrointestinal use. Such an influx of water may also serve to dilute the contrast medium, necessitating the administration of a higher dose of active ingredient to achieve the desired contrast enhancement effect, thereby increasing possible toxicity. With a hypoosmotic contrast medium, as described herein, many of these undesired effects may be eliminated or minimized, providing a preferred and highly effective contrast medium for magnetic resonance imaging.

As those skilled in the art will recognize, the osmolarity of a solution may be controlled by regulating the use of osmotically active materials in the contrast medium formulation. Osmotically active materials include such physiologically compatible compounds as monosaccharide sugars or sugar alcohols, disaccharide sugars, amino acids, and various synthetic compounds. Suitable monosaccharide sugars or sugar alcohols include, for example, erythrose, threose, ribose, arabinose, xylose, lyxose, allose, altrose, glucose, mannose, idose, galactose, talose, ribulose, fructose, sorbitol, mannitol, and sedoheptulose, with preferable monosaccharides being fructose, mannose, xylose, arabinose, mannitol and sorbitol. Suitable disaccharide sugars include, for example, lactose, sucrose, maltose, and cellobiose. Suitable amino acids include, for example, glycine, serine, threonine, cysteine, tyrosine, asparagine, glutamine, aspartic acid, glutamic acid, lysine, arginine and histidine. Synthetic compounds include, for example, propylene glycol, polypropylene glycol, ethylene glycol, polyethylene glycol and polyvinylpyrrolidone. Various other suitable osmotically active materials are well known to those skilled in the art, and are intended to be within the scope of the term osmotically active agent as used herein. Typically, to achieve the preferred ranges of osmolarity in the contrast medium of the invention, less than about 25 g/l, more preferably less than about 20 g/l, even more preferably less than about 15 g/l, and still more preferably less than about 10 g/l of the osmotically active materials are employed, and in some instances no osmotically active materials are employed. A most preferred range of osmotically active materials is generally between about 1 and about 10 g/l.

Although the most desirable pH of the contrast medium of the present invention may vary, as those skilled in the art will recognize, the preferred pH range for most diagnostic uses is generally between about 3 and about 10 pH units, more preferably between about 5 and 8 pH units. The desired pH can be achieved and maintained through the use of physiologically compatible pH regulating additives such as suitable bases, buffers, and the like, as one skilled in the art will recognize. Particularly preferred bases include sodium bicarbonate and sodium hydroxide, especially sodium bicarbonate. Particularly preferred buffers include sodium acetate and glacial acetic acid buffer.

The present invention is useful in imaging a patient generally, and/or in specifically diagnosing the presence of diseased tissue in a patient. The imaging process of the present invention may be carried out by administering a contrast medium of the invention to a patient, and then scanning the patient using magnetic resonance imaging to obtain visible images of an internal region of a patient and/or of any diseased tissue in that region. By region of a patient, it is meant the whole patient or a particular area or portion of the patient. The contrast medium is particularly useful in providing images of the gastrointestinal region, but can also be employed more broadly such as in imaging the vasculature or in other ways as will be readily apparent to those skilled in the art. The phrase gastrointestinal region or gastrointestinal tract, as used herein, includes the region of a patient defined by the esophagus, stomach, small and large intestines and rectum. The phrase vasculature, as used herein, denotes the blood vessels in the body or in an organ or part of the body. The patient can be any type of animal or mammal, but most preferably is a human.

As one skilled in the art would recognize, administration may be carried out in various fashions, such as intravascularly, orally, rectally, etc., using a variety of dosage forms. When the region to be scanned is the gastrointestinal region, administration of the contrast medium of the invention is preferably carried out orally or rectally. The useful dosage to be administered and the particular mode of administration will vary depending upon the age, weight and the particular mammal and region thereof to be scanned, and the particular medium of the invention to be employed. Typically, dosage is initiated at lower levels and increased until the desired contrast enhancement is achieved. Various combinations of biocompatible polymers may be used to modify the relaxation behavior of the medium or to alter properties such as the viscosity, osmolarity or palatability (in the case of orally administered materials). In carrying out the method of the present invention, the contrast medium can be used alone, or in combination with other diagnostic, therapeutic or other agents. Such other agents include excipients such as physiologically compatible flavoring or coloring materials. Particularly preferred flavoring agents include sucrose and/or natural citrus flavor. In addition, if desired, the contrast media of the invention may be encapsulated in liposomes or in other suitable delivery vehicles. The polymer or polymer and contrast agent and/or gas admixture may be sterilized by autoclaving prior to use, if desired.

The magnetic resonance imaging techniques which are employed are conventional and are described, for example, in D. M. Kean and M. A. Smith, *Magnetic Resonance Imaging: Principles and Applications*, (William and Wilkins, Baltimore 1986). Contemplated MRI techniques include, but are not limited to, nuclear magnetic resonance (NMR) and electronic spin resonance (ESR). The preferred imaging modality is NMR.

As will be apparent to those skilled in the art, the polymer or polymer admixture with contrast agent and/or gas, when employed in magnetic resonance imaging, may operate as a T1, T2 or proton density contrast medium, depending upon the type of polymer used, the molecular weight of the polymer, the concentration of the polymer, the type of contrast agent mixed with the polymer, the type of MRI modality chosen, and the details of the pulse sequence employed for MRI imaging, and all such mechanisms of operation are considered to be within the ambit of the present invention.

The media of the present invention have been shown to be extremely useful as contrast enhancement media in magnetic resonance imaging, particularly in imaging of the gastrointestinal region. By employing the polymers alone or by combining a contrast agent with the polymers in accordance with the present invention, lower overall concentrations of the contrast agents may be used to achieve the same, or in many cases a better degree of, contrast enhancement results. This has benefits not only in terms of toxicity, by avoiding the use of large amounts of the potentially toxic contrast agents, but also in terms of cost, since less of the often more expensive conventional contrast agents are used. Furthermore, in the case of negative contrast agents based on superparamagnetic particles, magnetic susceptibility artifacts will be reduced through the ability to use a lower dose of the contrast agent. These and other advantages described herein of the present invention will be readily apparent to those skilled in the art, upon reading the present disclosure.

A particularly preferred formulation of the contrast medium of the invention which is useful in magnetic resonance imaging is an aqueous solution of the following components:

(i) 5–10 g/l polygalacturonic acid having a weight average molecular weight of less than 30,000;

(ii) 20–70 mg/l Mn(II);

(iii) 0.5–3.0 g/l xanthan gum;

(iv) 2–6 g/l sodium bicarbonate;

(v) 2–6 g/l glacial acetic acid or sodium acetate buffer;

(vi) 2–6 g/l glycine; and, optionally, (vii) a flavorant selected from the group consisting of sucrose and natural citrus flavor. The pH of the above referenced formulation is preferably between about 5 and 8 pH units, and the formulation preferably has an osmolarity of between about 250 to about 260 milliosmoles/liter.

The present invention is further described in the following Examples. These Examples are not to be construed with as limiting the scope of the appended Claims.

EXAMPLES

Example 1

The polymer polyethylene glycol (PEG), having a molecular weight about 8000, was dissolved in water to various concentrations (w/w; by weight). To some of the aqueous PEG solutions was then added the contrast agent Gd-DTPA, such that the final concentration of Gd-DTPA was 1 mM. The relaxivity or relaxation rate (1/T1 and 1/T2) of the PEG and the PEG and Gd-DTPA solutions was then tested in vitro using a Toshiba MR-50A 0.5 Tesla (T) whole body scanner. The results are shown in Table 1 and FIG. 2. As the results indicate, in the presence of PEG the relaxivity of both water and Gd-DTPA is increased.

Figure 2:
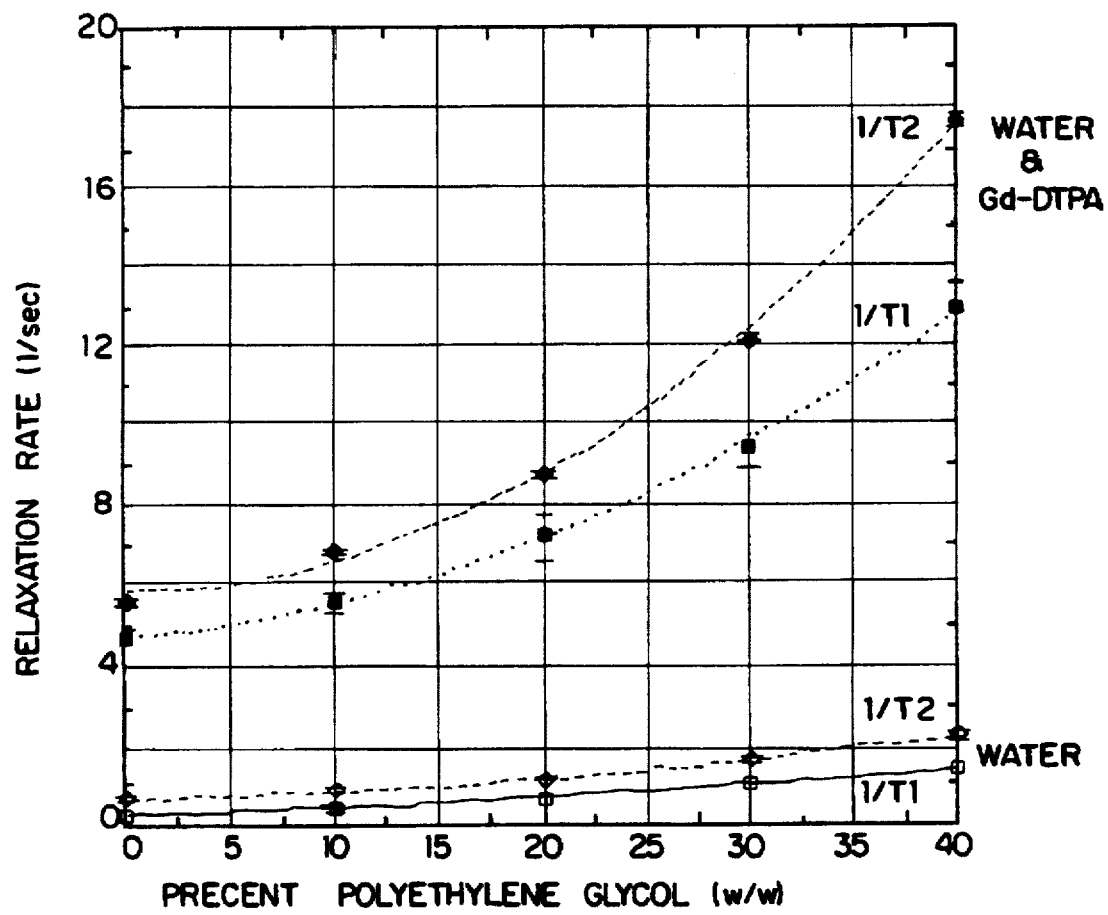
FIG. 2 is a graph of relaxation rate (1/sec) versus percent polyethylene glycol (w/w), wherein the polyethylene glycol polymer is in aqueous solution both with and without a Gd-DTPA contrast agent.

At best, it would be expected that the relaxation rates would be simply additive, i.e. the relaxation rate observed would be the sum of the relaxation rates of the individual components. However, an inspection of Table 1 and FIG. 2 shows that the 1/T1 relaxation rate of 40% (w/w) PEG 8000 in water was 1.35±0.04 at 0.5 T and the 1/T1 relaxation rate for 1 mM Gd-DTPA in water was measured to be 4.68±0.09 at 0.5 T. If the rates were simply additive it would be expected that the observed relaxation rate for 1 mM Gd-DTPA in a 40% (w/w) PEG 8000 solution would be approximately 4.68+1.35=6.03, at 0.5 T. The results in Table 1 and FIG. 2, however, surprisingly reveal that the relaxation rate for the PEG/water/Gd-DTPA mixture was in fact 12.81±0.72 at 0.5 T. In sum, for both T1 and T2 relaxation rates, it has been observed that the relaxation rate of the polymer/Gd-DTPA admixture is greater than the sum of the relaxation rates of the PEG solution and the Gd-DTPA solution alone.

The foregoing result is in hindsight believed to arise as a consequence of the exclusion of the Gd-DTPA from the immediate environment of the PEG molecules so that the effective concentration of the Gd-DTPA is increased in the water not bound to the polymer. However, the present invention is not intended to be limited by any theory of operation.

TABLE 1

Relaxivities at 0.5 T for PEG 8000/Water Mixtures
In the Absence and Presence of 1 mM Gd-DTPA

| Sample | 1/T1 (1/sec) | 1/T2 (1/sec) |
| --- | --- | --- |
| water | 0.21 ± 0.04 | 0.65 ± 0.04 |
| 10% PEG/water | 0.41 ± 0.03 | 0.85 ± 0.03 |
| 20% PEG/water | 0.64 ± 0.02 | 1.12 ± 0.06 |
| 30% PEG/water | 0.96 ± 0.02 | 1.57 ± 0 05 |
| 40% PEG/water | 1.35 ± 0.04 | 2.25 ± 0:08 |
| 1 mM Gd-DTPA/water | 4.68 ± 0.18 | 5.65 ± 0.03 |
| 10% PEG/water/1 mM Gd-DTPA | 5.58 ± 0.23 | 6.86 ± 0.02 |
| 20% PEG/water/1 mM Gd-DTPA | 7.19 ± 0.53 | 8.69 ± 0.07 |
| 30% PEG/water/1 mM Gd-DTPA | 9.42 ± 0.58 | 12.11 ± 0.08 |
| 40% PEG/water/1 mM Gd-DTPA | 12.81 ± 0.72 | 17.62 ± 0.15 |

Example 2

Figure 3:
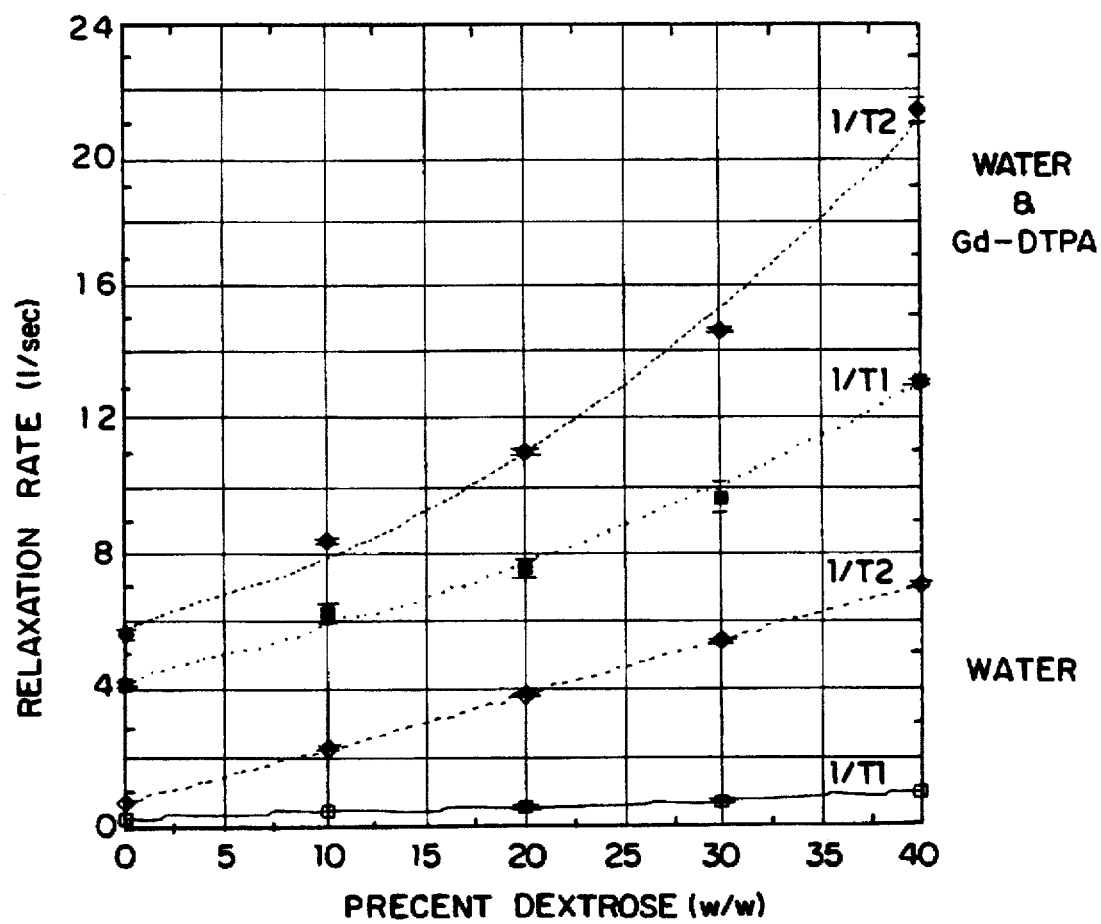
FIG. 3 is a graph of relaxation rate (1/sec) versus percent dextrose (w/w), wherein the dextrose polymer is in aqueous solution both with and without a Gd-DTPA contrast agent.

Example 1 was substantially repeated, except that the polymer dextrose was employed instead of PEG. The results are shown in FIG. 3. As the results indicate, in the presence of dextrose the relaxivity of both water and Gd-DTPA is increased.

As FIG. 3 illustrates, again, as with PEG, the relaxivity of the dextrose and Gd-DTPA solution is larger than the sum of the individual relaxation rates.

Example 3

Example 1 was substantially repeated except that an aqueous solution of 1 mM Gd-DTPA, 30% (w/w) PEG 8000 and 10% (w/w) dextrose was prepared and T1 was reported. A 1/T1 relaxivity or relaxation rate of 11.67±1.09 (1/sec) at 0.5 T was observed.

Examples 1, 2 and 3 show that different polymers may be used to preferentially alter the T1 or T2 relaxation rates of a solution. For example, as shown in Example 3, a solution of 1 mM Gd-DTPA and 30% PEG 8000 and 10% dextrose exhibits a T1 relaxation rate of 11.67±1.09 (1/sec) at 0.5 T. By comparison, 1 mM Gd-DTPA and 30% PEG 8000 in solution exhibits a T1 relaxation rate of 9.42±0.58 (1/sec) at 0.5 T, and 1 mM Gd-DTPA and 10% dextrose in solution exhibits a T1 relaxation rate of 2.33±0.02 (1/sec) at 0.5 T.

Example 4

Example 1 was substantially repeated, except that 10% (w/w) cellulose, a low toxicity polymer that is not degraded within the gastrointestinal tract, was employed, in aqueous solution with and without different concentrations of a ferrite contrast agent and with and without carbon dioxide gas.

Figure 4:
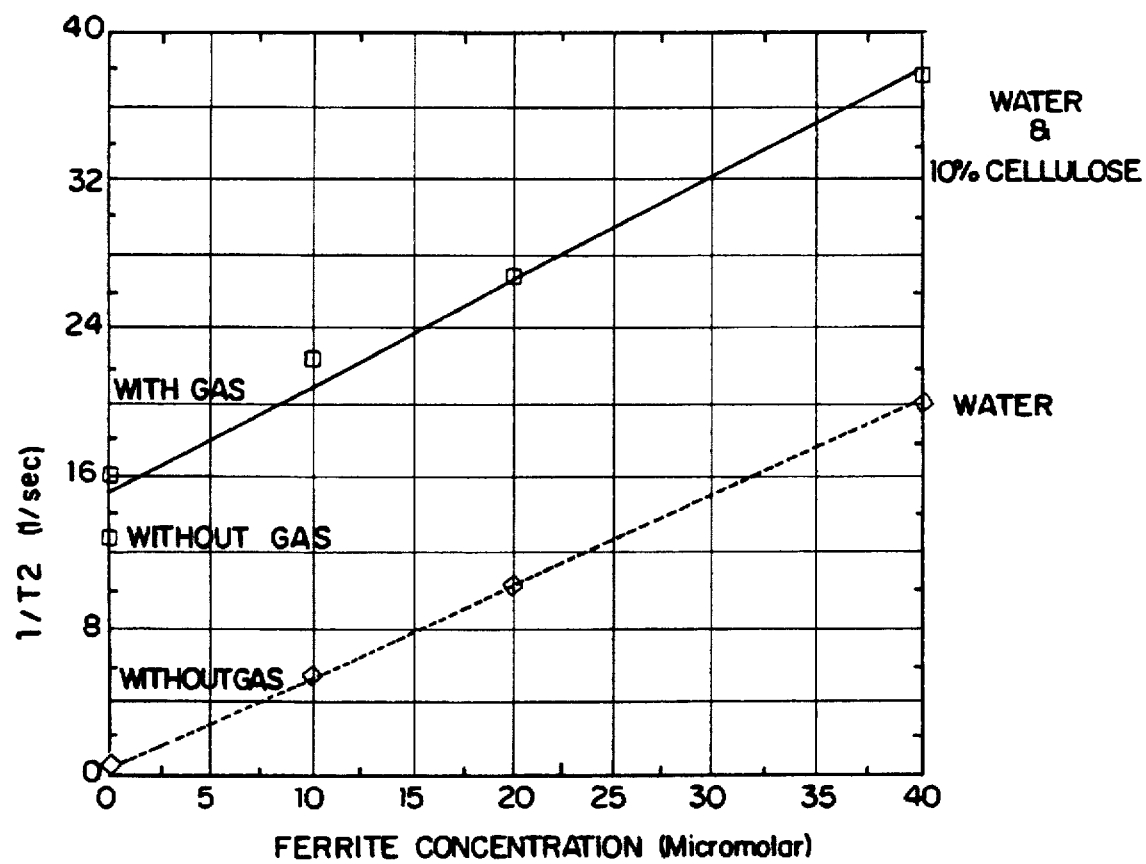
FIG. 4 is a graph of transverse relation rate 1/T2 (1/sec) versus ferrite concentration (micromolar), wherein the ferrite contrast agent is in aqueous solution with and without a cellulose polymer (and wherein the cellulose polymer is present with and without carbon dioxide gas).

The results are shown in Table 2 and FIG. 4. As the results indicate, cellulose is also an efficient T2 relaxation agent, and the T2 relaxivity of cellulose may be improved by mixing with a gas such as carbon dioxide. In addition, the results show that cellulose may be combined with a superparamagnetic contrast agent such as ferrites such that the combined polymer/ferrite contrast agent, whether mixed with gas or not, is superior in terms of relaxivity, as compared with either the polymer or ferrite alone. Specifically, from the results, it can be seen that the T2 relaxivity for a sample containing 10% cellulose with 10 mM ferrites after treating with gas has a higher T2 relaxivity than a 40 mM dispersion of ferrites in water. The immediate conclusion is that it would be possible to reduce the dose of ferrites administered by at least a factor of 4 and still obtain the same degree of contrast enhancement. This would have clear benefits in terms of decreasing the potential toxicity of the contrast agent.

TABLE 2

Relaxivities at 0.5 T for Water/Ferrite
and Cellulose/Water/Ferrite mixtures

| Sample | 1/T1 (1/sec) | 1/T2 (1/sec) |
| --- | --- | --- |
| water | 0.27 ± 0.05 | 0.55 ± 0.06 |
| +10 mM ferrites | 1.16 ± 0.01 | 5.45 ± 0.07 |
| +20 mM ferrites | 1.92 ± 0.03 | 10.20 ± 0.10 |
| +40 mM ferrites | 3.60 ± 0.10 | 20.24 ± 0.43 |
| 10% cellulose in water | — | 12.76 ± 0.08 |
| +pressurized with gas | 0.76 ± 0.01 | 15.95 ± 0.05 |
| gas + 10 mM ferrites | 1.98 1 0.03 | 22.82 ± 0.62 |
| gas + 20 mM ferrites | 2.41 ± 0.03 | 26.75 ± 0.32 |
| gas + 40 mM ferrites | 4.15 ± 0.11 | 37.42 ± 0.94 |

Example 5

A 2% aqueous solution of the polymer poly-galacturonic acid in admixture Mn(II) was prepared. The relaxivity (1/T1 and 1/T2) of the solution was then tested in vitro using a Toshiba MRT-50A 0.5 Tesla (T) whole body scanner. The 1/T1 was measured at 41.0±1.92 mmol$^{-1}$ sec$^{-1}$, and the 1/T2 was measured at 79.41±3.20 mmol$^{-1}$ sec$^{-1}$.

Example 6

A 0.5% aqueous solution of the polymer poly-galacturonic acid was prepared. To the solution was then added 0.1 mM Mn(II). The relaxivity (1/T1 and 1/T2) of the solution was tested in vitro using a Toshiba MRT-50A 0.5 Tesla (T) whole body scanner. The 1/T1 was measured at 1.20±0.056 sec$^{-1}$, and the 1/T2 was measured at 4.78±0.001 sec$^{-1}$.

Example 7

The procedures of Example 6 were substantially followed, except that sodium hydroxide was added to the solution in an amount sufficient to raise the pH from 2 (as in Example 6), to a pH of 4, 6, 7, and 8, respectively. The relaxivity (1/T1 and 1/T2) of the solutions at these various pH levels was tested in vitro using a Toshiba MRT-50A 0.5 Tesla (T) whole body scanner. The results are shown below in Table 3.

TABLE 3

Relaxivities at 0.5 T For
Water/Polygalacturonic Acid/Mn (II) Mixtures
At Varying pH Levels

| Sample pH | 1/T1 (1/sec) | 1/T2 (1/sec) |
|---|---|---|
| pH 4 | 4.15 ± 0.21 | 6.78 ± 0.14 |
| pH 6 | 4.10 ± 0.19 | 7.94 ± 0.32 |
| pH 7 | 3.73 ± 0.22 | 6.29 ± 0.24 |
| pH 8 | 4.11 ± 0.55 | 6.64 ± 0.27 |

Example 8

Aqueous samples of several different compounds chelated to or in admixture with Mn(II) were prepared. In the aqueous samples, the concentration of galacturonate monomer was 0.5%, the concentration of algin was 0.5%, and the concentration of cellulose was 0.25%. The relaxivity or relaxation rate of each was then tested in vitro using a Toshiba MRT-50A 0.5 Tesla (T) whole body scanner. The results are shown as R1 and R2 values, which represents relaxivities per concentration of Mn(II), that is, relaxivity per mmol$^{-1}$ liter sec$^{-1}$ (1/T1 mmol$^{-1}$ liter sec$^{-1}$; 1/T2 mmol$^{-1}$ liter sec$^{-1}$). R1 and R2 thus define the effect of the compounds on relaxivity for a standard concentration of Mn(II). The results are shown below in Table 4.

As revealed by Table 4, Mn(II), as manganese chloride, has an 1/T1 and 1/T2 relaxivity of about 8 and 39 respectively. The chelate of Mn(II), manganese N,N"-bis-carboxyamido-methyl-N-(2-methoxyethylene)-ethylenediamine-N,N'-diacetate (Mn(II)-EDTA-MEA), has a significantly lower relaxivity, with an 1/T1 and 1/T2 of about 3 and 8 respectively. The monomer of galacturonate has virtually no effect on the relaxivity of Mn(II). On the other hand, the Mn(II)/algin and Mn(II)/cellulose contrast media of the invention, were found to provide significant and unexpected improvement in relaxivity over Mn(II), Mn(II)-EDTA-MEA and Mn(II) galacturonate monomer, as shown in Table 4.

TABLE 4

Relaxivities at 0.5 T For Various
Mn(II)-Containing Aqueous Samples

| Sample | R1 | R2 |
|---|---|---|
| MnCl$_2$ | 8.73 ± 0.28 | 39.45 ± 0.52 |
| Mn-EDTA-MEA Chelate | 3.04 ± 0.15 | 7.98 ± 0.23 |
| MnCl$_2$ and Galacturonate Monomer Admixture | 9.01 ± 0.41 | 37.36 ± 0.10 |
| MnCl$_2$ and Algin Admixture | 20.3 ± 1.95 | 40.20 ± 0.38 |
| MnCl$_2$ and Cellulose Admixture | 21.00 ± 0.63 | 31.0 ± 1.20 |

Example 9

Aqueous samples of polygalacturonic acid of varying molecular weights and pectin, in admixture with manganese, were prepared. High molecular weight polygalacturonic acid having a weight average molecular weight of about 40,000, was obtained from Fluka Chemical Co., Ronkonkoma, N.Y. Low methoxy pectin, D075-X Apple Pectin, was obtained from Spreda Corp., Prospect Ky. Decagalacturonic acid (10 galacturonic acid monomer units) having a weight average molecular weight of about 1,900, was prepared by substantially following the procedures of Lakatos et al., U.S. Pat. No. 4,225,592. Low molecular weight polygalacturonic acid, having a weight average molecular weight of about 2,200, was prepared by hydrolyzing the low methoxy pectin (D075-X Apple Pectin, obtained from Spreda Corp., Prospect Ky.) substantially following the procedures of Mihashi, Pharmaceutical J., Vol. 81, pp. 1000–1002 (1961). Decagalacturonic acid (40%) and high molecular weight polygalacturonic acid (60%) were also mixed together to form a polygalacturonic acid composition having a weight average molecular weight of about 25,000. All polymer compositions were formulated to 0.6% polymer concentration.

Each polymer was then mixed with a 1 mM concentration of Mn(II). Samples were serially diluted with deionized water to give concentrations from 0.0125 to 0.5 mM Mn(II) and relaxivity (1/T1 and 1/T2) was tested vitro using a Toshiba MRT-50A 0.5 Tesla (T) whole body scanner. Relaxivity results were regressed against concentration to determine R1 and R2 (1/T1 mmol$^{-1}$ liter sec$^{-1}$; 1/T2 mmol$^{-1}$ liter sec$^{-1}$. The results are shown below in Table 5.

As revealed by Table 5, better relaxivity is achieved with manganese in admixture with low molecular weight polygalacturonic acid polymers (below 30,000 weight average molecular weight), than with higher weight polygalacturonic acid polymers. Also, as the data shows, polygalacturonic acid provides better relaxivity than pectin, when admixed with manganese.

TABLE 5

Relaxivities at 0.5 T For Aqueous Samples of
Pectin and Polygalacturonic Acids With Mn(II)

| Sample | R1 | R2 |
|---|---|---|
| Decagalacturonic Acid and Mn(II) | 35.33 ± 0.62 | 61.02 ± 0.89 |
| Low MW Polygalacturonic Acid and Mn(II) | 46.11 ± 0.35 | 67.98 ± 1.26 |
| 40% Decagalacturonic Acid and 60% High MW Polygalacturonic Acid and Mn(II) | 42.62 ± 0.29 | 67.28 ± 0.46 |
| Low Methoxy Pectin and Mn(II) | 16.53 ± 0.88 | 36.53 ± 0.69 |
| High MW Polygalacturonic Acid and Mn(II) | 28.99 ± 0.04 | 55.32 ± 1.11 |

Example 10

Two formulations of contrast media were prepared using different molecular weights of polygalacturonic acid. For one formulation, high molecular weight polygalacturonic acid having a weight average molecular weight of about 40,000, obtained from Fluka Chemical Co., Ronkonkoma, N.Y., was used. For the second formulation, low molecular weight polyglacturonic acid having a weight average molecular weight of about 2,200, was prepared by hydrolyzing the low methoxy pectin (D075-X Apple Pectin, obtained from Spreda Corp., Prospect Ky.) substantially following the procedures of Mihashi; Pharmaceutical J., Vol. 81, pp. 1000–1002 (1961). Specifically, to prepare the low molecular weight polygalacturonic acid, ten grams of the DO75-X Apple Pectin was hydrolyzed in 100 ml of a 5% HCl solution for 5 hours at a constant temperature of 85° C.

The solution was then vacuum filtered resulting in a dark brown precipitate and a yellow-colored solution. A decolorization step was then carried out as follows. First, two grams of activated charcoal were added to the solution and the solution heated to 80° C. for 30 minutes. The mixture was filtered, resulting in a clear colorless solution. The colorless solution was then evaporated to dryness resulting in the desired low molecular weight polygalacturonic acid as a yellow-brown powder.

The high and low molecular weight poly-galacturonic acid polymers were each formulated as an aqueous solution as shown in Table 6 below, to form hypoosmotic solutions having an osmolarity of between 220 and 260 milliosmoles/liter.

TABLE 6

Aqueous Formulations of Mn(II) With High and Low Molecular Weight Polygalacturonic Acids

| Ingredient | Amount |
| --- | --- |
| Polygalacturonic Acid (high or low MW, as described above) | 6 g/l |
| Mn$^{+2}$ (as MnCl$_2$) (ACS) (obtained from Spreda Corp., Prospect, KY) | 50 mg/l |
| Xanthan Gum (0.100%) (Keltrol RD NF, obtained from Kelco, Division of Merck, San Diego, CA) | 1 g/l |
| Sodium Bicarbonate (1 M; USP/NF) (obtained from Spectrum Pharmaceuticals,, Gardena, CA) | ≈50 ml (to raise pH to 6.0) |
| Glacial acetic acid (300 mM; USP/NF) (obtained from Spectrum Pharmaceuticals, Gardena, CA | 30 ml |
| Propylene Glycol (obtained from Spectrum Pharmaceuticals, Gardena, CA) | 2 g/l |
| Natural Citrus Flavoring (obtained from Firmenich, SA, Geneva, Switzerland) | 2 g/l |

Relaxivity (1/T1 and 1/T2) for each formulation was tested in vitro using a Toshiba MRT-50A 0.5 Tesla (T) whole body scanner. Relaxivity results were regressed against concentrations of Mn(II) to determine R1 and R2 (1/T1 mmol$^{-1}$ liter sec$^{-1}$; 1/T2 mmol$^{-1}$ liter sec$^{-1}$) for each formulation. The results are shown below in Table 7.

As revealed by Table 7, although the relaxivity of both formulations is excellent, the low molecular weight polygalacturonic acid formulation provided even better relaxivity than its high molecular weight counterpart.

TABLE 7

Relaxivities at 0.5 T For Aqueous Formulations of Mn(II) With High and Low Molecular Weight Polygalacturonic Acids

| Formulation | R1 | R2 |
| --- | --- | --- |
| High MW Polygalacturonic Acid Formulation | 28.99 ± 0.56 | 55.32 ± 1.11 |
| Low MW Polygalacturonic Acid Formulation | 37.4 ± 1.45 | 69.5 ± 1.37 |

Various modifications of the invention in addition to those shown and described herein will be apparent to those skilled in the art from the foregoing description. Such modifications are also intended to fall within the scope of the appended Claims.

What is claimed is:

1. A contrast medium for use in magnetic resonance imaging of a patient comprising an aqueous solution or suspension of a biocompatible polymer in admixture with a contrast agent, said contrast medium further comprising a biocompatible gas, wherein the contrast medium is hypoosmotic to bodily fluids of the patient.

2. A contrast medium of claim 1 wherein the hypoosmotic contrast medium has an osmolarity of less than 280 milliosmoles/liter.

3. A contrast medium of claim 2 wherein the osmolarity is between about 200 and about 270 milliosmoles/liter.

4. A contrast medium of claim 3 wherein the osmolarity is between about 220 and about 260 milliosmoles/liter.

5. A contrast medium of claim 4 wherein the osmolarity is between about 250 and about 260 milliosmoles/liter.

6. A contrast medium of claim 1 wherein the polymer is a natural polymer.

7. A contrast medium of claim 1 wherein the polymer is a synthetic polymer.

8. A contrast medium of claim 1 wherein the polymer is a polysaccharide.

9. A contrast medium of claim 1 wherein the polymer is a polyuronic acid.

10. A contrast medium of claim 1 wherein the polymer has a weight average molecular weight of less than 30,000.

11. A contrast medium of claim 1 wherein the polymer is a polysaccharide selected from the group consisting of arabinans, fructans, fucans, galactans, galacturonane, glucans, mannans, xylans, levan, fucoidan, carrageenan, galactocarolose, pectin, pectic acid, amylose, pullulan, glycogen, amylopectin, cellulose, carboxylmethylcellulose, hydroxypropylmethylcellulose, dextran, pustulan, chitin, agarose, keratan, chondroitin, dermatan, hyaluronic acid, alginic acid, and polysaccharides containing at least one aldose, ketose, acid or amine selected from the group consisting of erythrose, threose, ribose, arabinose, xylose, lyxose, allose, altrose, glucose, mannose, gulose, idose, galactose, talose, erythrulose, ribulose, xylulose, psicose, fructose, sorbose, tagarose, glucuronic acid, gluconic acid, glucaric acid, galacturonic acid, mannuronic acid, glucosamine, galactosamine and neuraminic acid.

12. A contrast medium of claim 1 wherein the polymer is selected from the group consisting of polyethylenes, polyoxyethylenes, polypropylenes, pluronic acids, pluronic alcohols, polyvinyls, and polyvinylpyrrolidones.

13. A contrast medium of claim 1 wherein the polymer is polygalacturonic acid.

14. A contrast medium of claim 1 wherein the polymer is polyethylene glycol.

15. A contrast medium of claim 1 wherein the contrast agent is selected from the group consisting of paramagnetic, superparamagnetic and proton density contrast agents.

16. A contrast medium of claim 15 wherein the contrast agent is a paramagnetic contrast agent which is a transition, lanthanide or actinide element.

17. A contrast medium of claim 16 wherein the paramagnetic contrast agent is selected from the group consisting of Gd(III), Mn(II), Cu(II), Cr(III), Fe(II), Fe(III), Co(II), Er(II), Ni(II), Eu(III) and Dy(III).

18. A contrast medium of claim 17 wherein the paramagnetic contrast agent is Mn(II).

19. A contrast medium of claim 1 wherein the contrast agent is a paramagnetic contrast agent which is bound to a complexing agent or to a proteinaceous macromolecule.

20. A contrast medium of claim 1 further comprising a suspending agent.

21. A contrast medium of claim 20 wherein the suspending agent is selected from the group consisting of xanthum gum, acacia, agar, alginic acid, aluminum mono-stearate, bassotin, karaya, gum arabic, unpurified bentonite, purified bentonite, bentonite magma, calcium carboxymethylcellulose, sodium carboxymethylcellulose, carrageenan, microcrystalline cellulose, dextran, gelatin, guar gum, hydroxyethylcellulose, hydroxypropylcellulose, hydroxypropylmethylcellulose, magnesium aluminum silicate, methylcellulose, pectin, casein, gelatin, polyethylene oxide, polyvinyl alcohol, povidone, propylene glycol, alginate, silicon dioxide, silicon dioxide colloidal, alginate, sodium alginate, and tragacanth.

22. A contrast medium of claim 21 wherein the suspending agent is xanthan gum.

23. A contrast medium of claim 1 further comprising an osmotically active material.

24. A contrast medium of claim 23 wherein the osmotically active material is selected from the group consisting of erythrose, threose, ribose, arabinose, xylose, lyxose, allose, altrose, glucose, mannose, idose, galactose, talose, ribulose, fructose, sorbitol, mannitol, sedoheptulose, lactose, sucrose, maltose, cellobiose, glycine, serine, threonine, cysteine, tyrosine, asparagine, glutamine, aspartic acid, glutamic acid, lysine, arginine, histidine, propylene glycol, polypropylene glycol, ethylene glycol, polyethylene glycol and polyvinylpyrrolidone.

25. A contrast medium of claim 24 wherein the osmotically active material is glycine.

26. A contrast medium of claim 1 further comprising a pH regulating additive effective to maintain a pH of between about 3 and about 10.

27. A contrast medium of claim 26 wherein the pH regulating additive is effective to maintain a pH of between about 3 and 8.

28. A contrast medium of claim 1 wherein the biocompatible gas is selected from the group consisting of air, oxygen, carbon dioxide, nitrogen, xenon, neon and argon.

29. A contrast medium of claim 1 further comprising a suspending agent, an osmotically active material, and a pH regulating additive effective to maintain a pH of between about 3 and about 10.

30. A contrast medium of claim 29 wherein the polymer is polygalacturonic acid having a weight average molecular weight of less than 30,000, the contrast agent is Mn(II), the suspending agent is xanthan gum, the osmotically active material is glycine, and the pH regulating additive is selected from the group consisting of sodium bicarbonate, glacial acetic acid and sodium acetate buffer, and wherein the contrast medium has an osmolarity of between about 200 and about 270 milliosmoles/ liter.

31. A contrast medium of claim 29 wherein the polymer is polygalacturonic acid having a weight average molecular weight of less than 30,000 in an amount between about 5 and about 10 grams/liter, the contrast agent is Mn(II) in an amount between about 20 and about 70 milligrams/liter, the suspending agent is xanthan gum in an amount between about 0.5 and about 3.0 grams/liter, the osmotically active material is glycine in an amount between about 2 and about 6 grams/liter, and the pH regulating additive is effective to maintain the pH between about 5 and about 8 and is a combination of sodium bicarbonate in an amount between about 2 and about 6 grams/liter and sodium acetate buffer in an amount between about 2 and about 6 grams/liter, and wherein the contrast medium has an osmolarity of between about 250 and about 260 milliosmoles/ liter.

32. A contrast medium of claim 1 which is a contrast medium for use in imaging a gastrointestinal region of a patient.

33. A contrast medium of claim 1 which is a contrast medium for use in imaging vasculature of a patient.

34. A method of providing an image of a internal region of a patient comprising (i) administering to the patient a diagnostically effective amount of a contrast medium comprising an aqueous solution or suspension of a biocompatible polymer in admixture with a contrast agent, said contrast medium further comprising a biocompatible gas, wherein the contrast medium is hypoosmotic to bodily fluids of the patient, and (ii) scanning the patient using magnetic resonance imaging to obtain visible images of the region.

35. A method of claim 34 wherein the region is the gastrointestinal region.

36. A method of claim 34 wherein the region is the vasculature.

37. A method of claim 34 wherein the hypoosmotic contrast medium has an osmolarity of less than 280 milliosmoles/liter.

38. A method of claim 37 wherein the osmolarity is between about 200 and about 270 milliosmoles/liter.

39. A method of claim 38 wherein the osmolarity is between about 220 and about 260 milliosmoles/liter.

40. A method of claim 39 wherein the osmolarity is between about 250 and about 260 milliosmoles/liter.

41. A method of claim 34 wherein the polymer is a natural polymer.

42. A method of claim 34 wherein the polymer is a synthetic polymer.

43. A method of claim 34 wherein the polymer is a polysaccharide.

44. A method of claim 34 wherein the polymer is a polyluronic acid.

45. A method of claim 34 wherein the polymer has a weight average molecular weight of less than 30,000.

46. A method of claim 34 wherein the polymer is a polysaccharide selected from the group consisting of arabians, fructans, fucans, galactans, galacturonans, glucans, mannans, xylans, levan, fucoidan, carrageenan, galactocarolose, pectin, pectic acid, amylose, pullulan, glycogen, amylopectin, cellulose, carboxylmethylcellulose, hydroxypropylmethylcellulose, dextran, pustulan, chitin, agarose, keratan, chondroitin, dermatan, hyaluronic acid, alginic acid, and polysaccharides containing at least one aldose, ketose, acid or amine selected from the group consisting of erythrose, threose, ribose, arabinose, xylose, lyxose, allose, altrose, glucose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid.

47. A method of claim 34 wherein the polymer is selected from the group consisting of polyethylenes, alcohols, polyvinyls, and polyvinylpyrrolidones, polyoxyethylenes, polypropylenes, pluronic acids, pluronic alcohols, polyvinyls, and polyvinylpyrrolidones.

48. A method of claim 34 wherein the polymer is polygalacturonic acid.

49. A method of claim 34 wherein the polymer is polyethylene glycol.

50. A method of claim 34 wherein the contrast agent is selected from the group consisting of paramagnetic, superparamagnetic and proton density contrast agents.

51. A method of claim 50 wherein the contrast agent is a paramagnetic contrast agent which is a transition, lanthanide or actinide element.

52. A method of claim 51 wherein the paramagnetic contrast agent is selected from the group consisting of Gd(III), Mn(II), Cu(II), Cr(III), Fe(II), Fe(III), Co(II), Er(II), Ni(II), Eu(III) and Dy(III).

53. A method of claim 52 wherein the paramagnetic contrast agent is Mn(II).

54. A method of claim 34 wherein the contrast agent is a paramagnetic contrast agent which is bound to a complexing agent or to a proteinaceous macromolecule.

55. A method of claim 34 further comprising a suspending agent.

56. A method of claim 55 wherein the suspending agent is selected from the group consisting of xanthum gum, acacia, agar, alginic acid, aluminum monostearate, bassotin, karaya, gum arabic, unpurified bentonire, purified bentonire, bentonire magna, calcium carboxymethylcellulose, sodium carboxymethylcellulose, carrageenan, microcrystalline cellulose, dextran, gelatin, guar gum, hydroxyethylcellulose, hydroxypropylcellulose, hydroxypropylmethylcellulose, magnesium aluminum silicate, methylcellulose, pectin, casein, gelatin, polyethylene oxide, polyvinyl alcohol, povidone, propylene glycol, alginate, silicon dioxide, silicon dioxide colloidal, alginate, sodium alginate, and tragacanth.

57. A method of claim 56 wherein the suspending agent is xanthan gum.

58. A method of claim 34 further comprising an osmotically active material.

59. A method of claim 58 wherein the osmotically active material is selected from the group consisting of erythrose, threose, ribose, arabinose, xylose, lyxose, allose, altrose, glucose, mannose, idose, galactose, talose, ribulose, fructose, sorbitol, mannitol, sedoheptulose, lactose, sucrose, maltose, cellubiose, glycine, serine, threonine, cysteine, tyrosine, asparagine, glutamine, aspartic acid, glutamic acid, lysine, arginine, histidine, propylene glycol, polypropylene glycol, ethylene glycol, polyethylene glycol and polyvinylpyrrolidone.

60. A method of claim 59 wherein the osmotically active material is glycine.

61. A method of claim 34 further comprising a pH regulating additive effective to maintain a pH of between about 3 and about 10.

62. A method of claim 61 wherein the pH regulating additive is effective to maintain a pH of between about 3 and 8.

63. A contrast medium of claim 34 wherein the biocompatible gas is selected from the group consisting of air, oxygen, carbon dioxide, nitrogen, xenon, neon and argon.

64. A method of claim 34 further comprising a suspending agent, an osmotically active material, and a pH regulating additive effective to maintain a pH of between about 3 and about 10.

65. A method of claim 64 wherein the polymer is polygalacturonic acid having a weight average molecular weight of less than 30,000, the contrast agent is Mn(II), the suspending agent is xanthan gum, the osmotically active material is glycine, and the pH regulating additive is selected from the group consisting of sodium bicarbonate, glacial acetic acid and sodium acetate buffer, and wherein the contrast medium has an osmolarity of between about 200 and about 270 milliosmoles/liter.

66. A method of claim 64 wherein the polymer is polygalacturonic acid having a weight average molecular weight of less than 30,000 in an amount between about 5 and about 10 grams/liter, the contrast agent is Mn(II) in an amount between about 20 and about 70 milligrams/liter, the suspending agent is xanthan gum in an amount between about 0.5 and about 3.0 grams/liter, the osmotically active material is glycine in an amount between about 2 and about 6 grams/liter, and the pH regulating additive is effective to maintain the pH between about 5 and about 8 and is a combination of sodium bicarbonate in an amount between about 2 and about 6 grams/liter and sodium acetate buffer in an amount between about 2 and about 6 grams/liter, and wherein the contrast medium has an osmolarity of between about 250 and about 260 milliosmoles/liter.

67. A method for diagnosing the presence of diseased tissue in a patient comprising (i) administering to the patient a diagnostically effective amount of a contrast medium comprising an aqueous solution or suspension of a biocompatible polymer in admixture with a contrast agent, said contrast medium further comprising a biocompatible gas, wherein the contrast medium is hypoosmotic to bodily fluids of the patient, and (ii) scanning the patient using magnetic resonance imaging to obtain visible images of any diseased tissue in the patient.

68. A method of claim 67 wherein the scanning is of the gastrointestinal region of the patient.

69. A method of claim 67 wherein the scanning is of the vasculature of the patient.

70. A method of claim 67 wherein said hypoosmotic contrast medium has an osmolarity of less than 280 milliosmoles/liter.

71. A method of claim 70 wherein said osmolarity is between about 200 and about 270 milliosmoles/liter.

72. A method of claim 71 wherein said osmolarity is between about 220 and about 260 milliosmoles/liter.

73. A method of claim 72 wherein said osmolarity is between about 250 and about 260 milliosmoles/liter.

74. A method of claim 67 wherein the polymer is a natural polymer.

75. A method of claim 67 wherein the polymer is a synthetic polymer.

76. A method of claim 67 wherein the polymer is a polysaccharide.

77. A method of claim 67 wherein the polymer is a polyuronic acid.

78. A method of claim 67 wherein the polymer has a weight average molecular weight of less than 30,000.

79. A method of claim 67 wherein the polymer is a polysaccharide selected from the group consisting of arabinans, fructans, fucans, galactans, galacturonans, glucans, mannans, xylans, levan, fucoidan, carrageenan, galactocarolose, pectin, pectic acid, amylose, pullulan, glycogen, amylopectin, cellulose, carboxylmethylcellulose, hydroxypropylmethylcellulose, dextran, pustulan, chitin, agarose, keratan, chondroitin, dermatan, hyaluronic acid, alginic acid, and polysaccharides containing at least one aldose, ketose, acid or amine selected from the group consisting of erythrose, threose, ribose, arabinose, xylose, lyxose, allose, altrose, glucose, mannose, gulose, idose, galactose, talose, erythrulose, ribulose, xylulose, psicose, fructose, sorbose, tagarose, glucuronic acid, gluconic acid, glucaric acid, galacturonic acid, mannuronic acid, glucosamine, galactosamine and neuraminic acid.

80. A method of claim 67 wherein the polymer is selected from the group consisting of polyethylenes, polyoxyethylenes, polypropylenes, pluronic acids, pluronic alcohols, polyvinyls, and polyvinylpyrrolidones.

81. A method of claim 67 wherein the polymer is polygalacturonic acid.

82. A method of claim 67 wherein the polymer is polyethylene glycol.

83. A method of claim 67 wherein the contrast agent is selected from the group consisting of paramagnetic, superparamagnetic and proton density contrast agents.

84. A method of claim 83 wherein the contrast agent is a paramagnetic contrast agent which is a transition, lanthanide or actinide element.

85. A method of claim 84 wherein the paramagnetic contrast agent is selected from the group consisting of Gd(III), Mn(II), Cu(II), Cr(III), Fe(II), Fe(III), Co(II), Er(II), Ni(II), Eu(III) and Dy(III).

86. A method of claim 85 wherein the paramagnetic contrast agent is Mn(II).

87. A method of claim 67 wherein the contrast agent is a paramagnetic contrast agent which is bound to a complexing agent or to a proteinaceous macromolecule.

88. A method of claim 67 further comprising a suspending agent.

89. A method of claim 88 wherein the suspending agent is selected from the group consisting of xanthum gum, acacia, agar, alginic acid, aluminum monostearate, bassotin, karaya, gum arabic, unpurified bentonire, purified bentonite, bentonire magma, calcium carboxymethylcellulose, sodium carboxymethylcellulose, carrageenan, microcrystalline cellulose, dextran, gelatin, guar gum, hydroxyethylcellulose, hydroxypropylcellulose, hydroxypropylmethylcellulose, magnesium aluminum silicate, methylcellulose, pectin, casein, gelatin, polyethylene oxide, polyvinyl alcohol, povidone, propylene glycol, alginate, silicon dioxide, silicon dioxide colloidal, alginate, sodium alginate, and tragacanth.

90. A method of claim 89 wherein the suspending agent is xanthan gum.

91. A method of claim 67 further comprising an osmotically active material.

92. A method of claim 91 wherein the osmotically active material is selected from the group consisting of erythrose, threose, ribose, arabinose, xylose, lyxose, allose, altrose, glucose, mannose, idose, galactose, talose, ribulose, fructose, sorbitol, mannitol, sedoheptulose, lactose, sucrose, melrose, cellobiose, glycine, serine, threonine, cysteine, tyrosine, asparagine, glutamine, aspartic acid, glutamic acid, lysine, arginine, histidine, propylene glycol, polypropylene glycol, ethylene glycol, polyethylene glycol and polyvinylpyrrolidone.

93. A method of claim 92 wherein the osmotically active material is glycine.

94. A method of claim 67 further comprising a pH regulating additive effective to maintain a pH of between about 3 and about 10.

95. A method of claim 94 wherein the pH regulating additive is effective to maintain a pH of between about 3 and 8.

96. A contrast medium of claim 67 wherein the biocompatible gas is selected from the group consisting of air, oxygen, carbon dioxide, nitrogen, xenon, neon and argon.

97. A method of claim 67 further comprising a suspending agent, an osmotically active material, and a pH regulating additive effective to maintain a pH of between about 3 and about 10.

98. A method of claim 97 wherein the polymer is polygalacturonic acid having a weight average molecular weight of less than 30,000, the contrast agent is Mn(II), the suspending agent is xanthan gum, the osmotically active material is glycine, and the pH regulating additive is selected from the group consisting of sodium bicarbonate, glacial acetic acid and sodium acetate buffer, and wherein the contrast medium has an osmolarity of between about 200 and about 270 milliosmoles/liter.

99. A method of claim 97 wherein the polymer is polygalacturonic acid having a weight average molecular weight of less than 30,000 in an amount between about 5 and about 10 grams/liter, the contrast agent is Mn(II) in an amount between about 20 and about 70 milligrams/liter, the suspending agent is xanthan gum in an amount between about 0.5 and about 3.0 grams/liter, the osmotically active material is glycine in an amount between about 2 and about 6 grams/liter, and the pH regulating additive is effective to maintain the pH between about 5 and about 8 and is a combination of sodium bicarbonate in an amount between about 2 and about 6 grams/liter and sodium acetate buffer in an amount between about 2 and about 6 grams/liter, and wherein the contrast medium has an osmolarity of between about 250 and about 260 milliosmoles/liter.

100. A contrast medium of claim 1 wherein the polymer is polygalacturonic acid having a weight average molecular weight of less than about 30,000.

101. A contrast medium of claim 100 wherein the contrast agent is Mn(II).

102. A method of claim 34 wherein the polymer is polygalacturonic acid having a weight average molecular weight of less than about 30,000.

103. A method of claim 102 wherein the contrast agent is Mn(II).

104. A method of claim 67 wherein the polymer is polygalacturonic acid having a weight average molecular weight of less than about 30,000.

105. A method of claim 104 wherein the contrast agent is Mn(II).

* * * * *

UNITED STATES PATENT AND TRADEMARK OFFICE
CERTIFICATE OF CORRECTION

PATENT NO. : 5,681,542
DATED : Oct. 28, 1997
INVENTOR(S) : Evan C. Unger

It is certified that error appears in the above-identified patent and that said Letters Patent is hereby corrected as shown below:

On page 2, second column, in the "OTHER PUBLICATIONS" section, at "Atkins", please delete "Atkins et a.," and insert --Atkins et al.,-- therefor.

In column 1, line 13, please delete "abandoned." and insert --abandoned, the disclosures of which are incorporated herein by reference in its entirety.--

In column 1, line 66, please delete "of the proton" and insert --or the proton-- therefor.

In column 5, line 59, please delete "poly-galacturonic" and insert --polygalacturonic-- therefor.

In column 7, line 31, please delete "bassotin," and insert --bassorin,-- therefor.

In column 7, line 32, please delete "purified bentonire," and insert --purified bentonite,-- therefor.

In column 7, line 33, please delete "bentonire magma," and insert --bentonite magma,-- therefor.

In column 12, Table 2, second column thereof, line 30, please delete "1.98 1 0.03" and insert --1.98 ± 0.03-- therefor.

UNITED STATES PATENT AND TRADEMARK OFFICE
CERTIFICATE OF CORRECTION

PATENT NO. : 5,681,542
DATED : Oct. 28, 1997
INVENTOR(S) : Evan C. Unger

It is certified that error appears in the above-identified patent and that said Letters Patent is hereby corrected as shown below:

In column 12, line 38, please delete "poly-galacturonic" and insert --polygalacturonic-- therefor.

In column 14, line 18, please delete "tested vitro" and insert --tested in vitro-- therefor.

In column 14, line 59, please delete "polyglacturonic" and insert --polygalacturonic-- therefor.

In column 16, claim 11, line 31, please delete "galacturonane," and insert --galacturonans-- therefor.

In column 18, claim 44, line 34, please delete "polyluronic" and insert --polyuronic-- therefor.

In column 18, claim 46, line 39, please delete "arabians," and insert --arabinans-- therefor.

In column 18, claim 47, lines 54-55, please delete "alcohols, polyvinyls, and polyvinylpyrrolidones,".

In column 19, claim 56, line 14, please delete "bassotin," and insert --bassorin,-- therefor.

In column 19, claim 56, line 15, please delete "unpurified bentonire, purified bentonire," and insert --unpurified bentonite, purified bentonite,-- therefor.

UNITED STATES PATENT AND TRADEMARK OFFICE
CERTIFICATE OF CORRECTION

PATENT NO. : 5,681,542
DATED : Oct. 28, 1997
INVENTOR(S) : Evan C. Unger

It is certified that error appears in the above-identified patent and that said Letters Patent is hereby corrected as shown below:

In column 19, claim 56, line 16, please delete "bentonire magna" and insert --bentonite magma,-- therefor.

In column 20, claim 79, line 54, please delete "tagarose," and insert --tagatose,-- therefor.

In column 21, claim 89, line 17, please delete "bassotin," and insert --bassorin,-- therefor.

In column 21, claim 89, line 18, please delete "unpurified bentonire," and insert --unpurified bentonite,-- therefor.

In column 21, claim 89, line 19, please delete "bentonire magma," and insert --bentonite magma,-- therefor.

In column 21, claim 92, line 36, please delete "melrose," and insert --maltose,-- therefor.

Signed and Sealed this

Eleventh Day of August 1998

Attest:

BRUCE LEHMAN

*Attesting Officer*   *Commissioner of Patents and Trademarks*